United States Patent
Amick et al.

(10) Patent No.: US 7,244,784 B2
(45) Date of Patent: Jul. 17, 2007

(54) AQUEOUS NANOPARTICLE DISPERSIONS

(75) Inventors: David Richard Amick, Doylestown, PA (US); Robert Howard Gore, Southampton, PA (US); Dennis Paul Lorah, Lansdale, PA (US); James Watson Neely, Dresher, PA (US)

(73) Assignee: Rohm and Haas Company, Philadelphia, PA (US)

( * ) Notice: Subject to any disclaimer, the term of this patent is extended or adjusted under 35 U.S.C. 154(b) by 133 days.

(21) Appl. No.: 10/452,175

(22) Filed: Jun. 2, 2003

(65) Prior Publication Data

US 2003/0232918 A1    Dec. 18, 2003

Related U.S. Application Data

(60) Provisional application No. 60/389,043, filed on Jun. 14, 2002.

(51) Int. Cl.
    *C08F 220/16* (2006.01)

(52) U.S. Cl. ............. 524/556; 524/560; 525/330.3; 525/327.8; 525/329.3

(58) Field of Classification Search ............ 524/556, 524/560, 525, 502, 515; 525/327.4, 377.8, 525/330.3, 327.8, 329.3
    See application file for complete search history.

(56) References Cited

U.S. PATENT DOCUMENTS

| | | | |
|---|---|---|---|
| 4,021,364 A | 5/1977 | Speiser et al. | |
| 4,403,003 A | 9/1983 | Backhouse | |
| 4,414,370 A | 11/1983 | Hamielec et al. | |
| 4,487,855 A | 12/1984 | Shih et al. | |
| 4,514,552 A | 4/1985 | Shay et al. | |
| 4,560,714 A | 12/1985 | Gajria et al. | |
| 4,623,692 A | 11/1986 | Hansen | |
| 4,746,455 A | 5/1988 | Matsuda et al. | |
| 4,777,213 A | 10/1988 | Kanda et al. | |
| 4,857,577 A * | 8/1989 | Buter | 524/458 |
| 5,149,745 A | 9/1992 | Owens et al. | |
| 5,212,251 A | 5/1993 | Lorah et al. | |
| 5,212,273 A | 5/1993 | Das et al. | |
| 5,290,654 A | 3/1994 | Sacripante et al. | |
| 5,320,711 A | 6/1994 | Dauplaiese et al. | |
| 5,468,801 A | 11/1995 | Antonelli et al. | |
| 5,494,954 A | 2/1996 | Das et al. | |
| 5,506,284 A | 4/1996 | McGee | |
| 5,536,771 A * | 7/1996 | Saito et al. | 524/460 |
| 5,538,717 A | 7/1996 | La Poterie | |
| 5,674,531 A | 10/1997 | Ahlers et al. | |
| 5,863,996 A | 1/1999 | Graham | |
| 5,874,111 A | 2/1999 | Maitra et al. | |
| 6,020,419 A | 2/2000 | Bock et al. | |
| 6,028,135 A * | 2/2000 | Keller et al. | 524/458 |
| 6,121,365 A * | 9/2000 | Saibara et al. | 524/458 |
| 6,194,530 B1 | 2/2001 | Klesse et al. | |
| 6,203,802 B1 | 3/2001 | Handjani et al. | |
| 6,268,222 B1 | 7/2001 | Chandler et al. | |
| 6,277,953 B1 * | 8/2001 | Nothnagel et al. | 528/489 |
| 6,329,446 B1 | 12/2001 | Sacripante et al. | |
| 6,387,519 B1 | 5/2002 | Anderson et al. | |
| 6,420,023 B1 * | 7/2002 | Rowley et al. | 428/355 CN |
| 6,646,041 B2 * | 11/2003 | St. John Williams et al. | 524/522 |
| 2002/0065208 A1 | 5/2002 | Aubay et al. | |
| 2002/0164297 A1 | 11/2002 | Ferrari et al. | |
| 2002/0177522 A1 | 11/2002 | Alexander, IV et al. | |
| 2002/0193521 A1 | 12/2002 | Cruz et al. | |
| 2003/0055178 A1 | 3/2003 | Gore et al. | |
| 2003/0059599 A1 * | 3/2003 | Beckley et al. | 428/327 |
| 2003/0162890 A1 | 8/2003 | Kalantar et al. | |

FOREIGN PATENT DOCUMENTS

| | | |
|---|---|---|
| EP | 1 245 587 A1 | 10/2002 |
| WO | WO 93/00376 | 1/1993 |
| WO | WO 93/24534 | 12/1993 |
| WO | WO 99/01522 | 1/1999 |
| WO | WO 00/59951 | 10/2000 |
| WO | WO 00/59953 | 10/2000 |
| WO | WO 01/43859 | 6/2001 |
| WO | WO 01/90226 | 11/2001 |
| WO | WO 02-18451 | 3/2002 |
| WO | WO 02/26895 | 4/2002 |
| WO | WO 0226895 A1 * | 4/2002 |

OTHER PUBLICATIONS

Dr. D. Horn and Dr. J. Rieger, Organic Nanoparticles in the Aqueous Phase—Theory, Experiment, and Use, Angew. Chem. Int. Ed. 2001, 40, pp. 4330-4361.

* cited by examiner

*Primary Examiner*—David W. Wu
*Assistant Examiner*—Satya B. Sastri
(74) *Attorney, Agent, or Firm*—Ronald D. Bakule; Kim R. Jessum

(57) ABSTRACT

New aqueous PNP dispersions are disclosed. A method of preparing an aqueous PNP dispersion from solvent-based PNPs having a diameter in the range of from 1 to 50 nanometers is disclosed. An associative thickener composition based on PNPs having an average of at least two phobes extending from the surface of said PNPs is also disclosed. The aqueous PNP dispersions are useful in aqueous-based industrial and consumer products, such as latex paint.

9 Claims, No Drawings

AQUEOUS NANOPARTICLE DISPERSIONS

CROSS REFERENCE TO RELATED PATENT APPLICATIONS

This is a non-provisional application of prior pending U.S. provisional application Ser. No. 60/389,043 filed Jun. 14, 2002.

The present invention relates to a method of preparing aqueous dispersions of crosslinked polymeric nanoparticles. The present invention also relates to aqueous dispersions of crosslinked polymeric nanoparticles and associative thickeners for aqueous-based products.

Crosslinked polymeric nanoparticles (hereinafter "PNPs") are a new class of macromolecular particles that are useful in a variety of consumer and industrial products, such as dispersants and rheology modifiers for aqueous-based latex emulsion paints.

There is a wide variety of consumer and industrial products in the form of thickened aqueous systems. Examples of such products are domestic or personal care products, such as detergents, shampoos, hair conditioners, liquid soaps or cosmetic fluids, dentifrices, domestic or industrial liquid cleaners, metal working fluids, latex paints, and various other coating materials. Such aqueous products often contain rheology modifiers, which thicken their flow characteristics.

Associative thickeners are a class of rheology modifiers that can provide improved flow properties (e.g., flow, leveling, sag resistance) to aqueous products, such as latex paints. Associative thickeners are typically water-soluble polymers having two or more attached hydrophobic blocks or branches ("phobes"). It is believed that the phobes inter-associate with each other to form a network. The resulting network is believed to contribute to the improved rheological properties.

Unfortunately, many associative thickeners are prepared as emulsion polymers using surfactants, which contribute to increased water-sensitivity of the resulting cured paint film. This causes a variety of problems, such as water spotting, streaking, blistering, reduced adhesion, and reduced scrub resistance. Accordingly, an object of the present invention is to prepare associative thickeners that do not require surfactants.

Unlike latex emulsions, which are typically prepared using surfactants in water to provide polymer particles having a mean particle size greater than 50 nanometers, dispersions of PNPs having a mean particle size in the range of from 1 to 50 nanometers can be synthesized without the use of surfactants by the free radical copolymerization of mono-ethylenically unsaturated monomers with multi-ethylenically unsaturated monomers in organic solvents. While it is desirable to minimize the use of surfactants in aqueous-based products, it is also desirable to reduce the presence of volatile organic solvents in such products, such as by replacement of organic solvent with water. Accordingly, there is presently a need to provide PNP dispersions containing water, which do not require the use of surfactants for imparting stability.

Many industrial and consumer products that can benefit from the addition of PNPs are water-based, such as water-based latex paint. However, combining organic solvent-based polymeric compositions (e.g., PNPs) with water-based products is fraught with problems. For example, although polymers are typically stable in the solvents they are prepared in, solvent-based polymers tend to destabilize (e.g., phase separate) upon combination with liquids that are poor solvents for the PNPs, such as water is for alkylacrylic-based PNPs. As a result, destabilized PNPs do not disperse well and tend to lose their effectiveness in aqueous-based products. Accordingly, there is presently a need to transform solvent-based PNP dispersions into aqueous-based PNP dispersions, which do not destabilize upon such transformation.

U.S. Pat. No. 5,290,654 discloses a process for the preparation of toner compositions that includes the steps of: dissolving a polymer in an organic solvent; dispersing the resulting solution in an aqueous media containing a surfactant; and stirring the mixture with optional heating to remove the organic solvent, thereby obtaining suspended polymer particles. While this patent mentions that said steps provide suspended polymer particles of about 0.05 micron (50 nanometers) to about 2 microns (2,000 nanometers) in volume diameter, the suspended polymer particles actually provided in the examples of this patent are based on non-crosslinked condensation polyesters having a volume diameter in the range of from 150 nanometers to 260 nanometers. In addition, the process for preparing the suspended polymer particles requires the use of surfactants.

U.S. Pat. No. 4,514,552 discloses the preparation of alkali soluble thickeners having improved water sensitivity, which are aqueous emulsion copolymers of an alpha, beta-mono-ethylenically unsaturated carboxylic acid, a monoethylenically unsaturated monomer lacking surfactant capacity, a nonionic urethane monomer which is the urethane reaction product of a monohydric nonionic surfactant with a mono-ethylenically unsaturated monoisocyanate, and a polyethylenically unsaturated monomer. The working example of this patent requires the use of a surfactant for preparing polymer particles having an average diameter of 92 nm, which are useful as aqueous thickeners.

Accordingly, neither of the aforementioned patents teach the preparation of aqueous-based PNP dispersions having an average particle size in the range of 1 to 50 nanometers. Moreover, both of the aforementioned patents require the use of surfactants for forming stable polymer particles in aqueous media.

The present inventors have discovered a method of preparing aqueous PNP dispersions, which do not require the use of surfactants to ensure stability (e.g., the particles remain substantially unflocculated). The PNPs of the present invention are initially prepared in solvent, and are subsequently converted into an aqueous medium. In the present invention, a dispersion of PNPs is prepared containing neutralizable polymerized units, which is optionally neutralized, and combined with water. The resulting PNP dispersion can be used as-is (i.e., containing both the solvent and the water), or can be used after subsequent removal of at least a portion of the solvent.

The present inventors have also discovered that dispersions of neutralized PNPs having an average of at least two phobes extending from the surface of each PNP can be used as rheology modifiers in aqueous-based formulations. Without being bound to a particular theory, it is believed that the phobes extending from the surface of the neutralized PNPs provide an "associative thickening" function. Because the crosslinking of the PNPs reduces their solubility in water, and the PNPs do not require the use of surfactants, it is believed that the neutralized PNP associative thickeners of the present invention reduce the aforementioned water sensitivity problems in cured aqueous-based latex coatings.

According to a first aspect of the present invention, there is provided a method of preparing an aqueous PNP dispersion, comprising the steps of:

(a) preparing a PNP dispersion, said PNP dispersion comprising:
  (i) PNPs having a diameter in the range of from 1 to 50 nanometers, said PNPs comprising as polymerized units at least one multi-ethylenically-unsaturated monomer and at least one neutralizable ethylenically-unsaturated monomer; and
  (ii) at least one solvent;
(b) neutralizing at least a portion of the neutralizable polymerized units formed from the at least one neutralizable ethylenically-unsaturated monomer with at least one neutralizing agent to form an at least partially neutralized PNP dispersion; and
(c) combining the at least partially neutralized PNP dispersion with an aqueous medium.

According to a second aspect of the present invention, there is provided an aqueous PNP dispersion, comprising:
  (a) PNPs having a diameter in the range of from 1 to 50 nanometers, said PNPs comprising as polymerized units at least one multi-ethylenically-unsaturated monomer and at least one neutralizable ethylenically-unsaturated monomer;
  (b) at least one neutralizing agent to partially neutralize the at least one neutralizable ethylenically-unsaturated monomer; and
  (c) an aqueous medium.

According to a third aspect of the present invention, there is provided a PNP dispersion, comprising:
  (a) PNPs having a diameter in the range of from 1 to 50 nanometers, said PNPs comprising as polymerized units at least one multi-ethylenically-unsaturated monomer and at least one neutralizable ethylenically-unsaturated monomer; and
  (b) at least one solvent, wherein the solvent is a good solvent for the PNPs and the solubility of the solvent in water is at least 10 weight percent.

According to a fourth aspect of the present invention, there is provided an associative thickener composition, comprising: PNPs having a diameter in the range of from 1 to 50 nanometers, said PNPs comprising as polymerized units at least one multi-ethylenically-unsaturated monomer and at least one neutralizable ethylenically-unsaturated monomer, and said PNPs comprising an average of at least two phobes extending from the surface of said PNPs.

As used herein, the term, "water-compatible solvent" refers to a solvent or a mixture of solvents that is at least partially soluble in water at the processing conditions. Water-compatible solvents include solvents that are fully miscible in water.

As used herein, the term "dispersion" refers to a physical state of matter comprising at least two distinct phases wherein one phase is distributed in the second phase, the second phase being continuous.

As used herein, the term "molecular weight", when describing the PNPs, refers to the apparent molecular weight one obtains using standard gel permeation chromatography methods, e.g., using THF solvent at 40 C, 3 Plgel Columns (Polymer Labs), 100 Angstrom, 10^3, 10^4 Angstroms, 30 cm long, 7.8 mm ID, 1 mil/min, 100 microliter injection volume, calibrated to narrow polystyrene standards using Polymer Labs CALIBRE™ software.

As used herein, the term "Tg" refers to the glass transition temperature as is determined using differential scanning calorimetry ("DSC") methods.

As used herein, the following abbreviations shall have the following meanings, unless the context clearly indicates otherwise: %=percent; C=centigrade; μm=micron; UV=ultraviolet; rpm=revolutions per minute; nm=nanometer; J=joules; cc=cubic centimeter; g=gram; wt %=weight percent; L=liter; mL=milliliter; MIAK=methyl iso-amyl ketone; MIBK=methyl iso-butyl ketone; BA=butyl acrylate; AA=acrylic acid; MAA=methacrylic acid; PS=particle size=mean particle diameter; PMA=poly(methyl acrylate); CyHMA=cyclohexylmethacrylate; EG=ethylene glycol; DPG=dipropylene glycol; DEA=diethylene glycol ethyl ether acetate; BzA=benzylacrylate; BzMA=benzyl methacrylate; MAPS=MATS=(trimethoxylsilyl)propylmethacrylate; OFPMA=octafluoropentyl methacrylate; PMA=propyl methacrylate; PETTA=pentaerythriol tetra/triacetate; PPG4000DMA=polypropyleneglycol 4000dimethacrylate; DPEPA=dipentaerythriol pentaacrylate; TMSMA=trimethylsilyl methacrylate; MOPTSOMS=methacryloxypropylbis(trimethylsiloxy)methylsilane; MOPMDMOS=3-methacryloxypropylmethyldimethoxysilane; TAT=triallyl-1,3,5-triazine-2,4,6-(1H, 3H,5H)-trione; IBOMA=isobornyl methacrylate; PGMEA=propyleneglycol monomethylether acetate; PEGMEMA475=poly(ethylene glycol methyl ether)methacrylate Mw=475; EUG=eugenol (4-allyl-2-methoxyphenol); and PGDMA=propyleneglycol dimethacrylate.

The term "(meth)acrylic" includes both acrylic and methacrylic and the term "(meth)acrylate" includes both acrylate and methacrylate. Likewise, the term "(meth)acrylamide" refers to both acrylamide and methacrylamide. "Alkyl" includes straight chain, branched and cyclic alkyl groups.

All ranges defined herein are inclusive and combinable.

The present invention is directed to a method of preparing aqueous PNP dispersions, in which the PNPs have a diameter in the range of from 1 to 50 nanometers. The present invention is also directed to providing associative thickener compositions including PNPs having a diameter in the range of from 1 to 50 nanometers.

While the PNPs used in the various embodiments of the present invention typically have a mean particle diameter in the range of from 1 nm to 50 nm, they preferably have a mean particle diameter in the range of from 1 nm to 40 nm, more preferably from 1 nm to 30 nm, even more preferably from 1 nm to 25 nm, even further preferably from 1 nm to 20 nm, and most preferably from 1 nm to 10 nm. It is further typical that the PNPs have a mean particle diameter of at least 1.5 nm, preferably at least 2 nm.

In the method of preparing the aqueous PNP dispersions of the present inventions, a PNP dispersion is first prepared, wherein the PNPs include as polymerized units at least one multi-ethylenically-unsaturated monomer and at least one neutralizable ethylenically-unsaturated monomer.

The PNPs can be formed by the free radical polymerization of at least one multi-ethylenically-unsaturated monomer and at least one neutralizable ethylenically-unsaturated monomer. Typically, unless specified otherwise, the amount of the at least one polymerized multi-ethylenically-unsaturated monomer is at least 1% by weight, based on the weight of the PNPs. Up to and including 100% polymerized multi-ethylenically-unsaturated monomer, based on the weight of the PNPs, can be effectively used in the particles of the present invention. It is preferred that the amount of polymerized multi-ethylenically-unsaturated monomer is from 1% to 80% based on the weight of the PNPs, more preferably from 1% to 60% based on the weight of the PNPs, and most preferably from 1% to 25% based on the weight of the PNPs. Typically, the amount of polymerized multi-ethylenically-unsaturated monomer is at least 1%, more typically at least 2%, further typically at least 3%, even more typically at least 5%, and further more typically at least 7.5% and most typically at least 10%.

Suitable multi-ethylenically-unsaturated monomers useful in the present invention include di-, tri-, tetra-, or higher multi-functional ethylenically unsaturated monomers such as, for example, trivinylbenzene, divinyltoluene, divinylpyridine, divinylnaphthalene and divinylxylene; and such as ethyleneglycol diacrylate, trimethylolpropane triacrylate, diethyleneglycol divinyl ether, trivinylcyclohexane, allyl methacrylate ("ALMA"), allyl acrylate, ethyleneglycol dimethacrylate ("EGDMA"), diethyleneglycol dimethacrylate ("DEGDMA"), propyleneglycol dimethacrylate, propyleneglycol diacrylate, trimethylolpropane trimethacrylate ("TMPTMA"), divinyl benzene ("DVB"), 2,2-dimethylpropane-1,3-diacrylate, 1,3-butylene glycol diacrylate, 1,3-butylene glycol dimethacrylate, 1,4-butanediol diacrylate, diethylene glycol diacrylate, diethylene glycol dimethacrylate, 1,6-hexanediol diacrylate, 1,6-hexanediol dimethacrylate, tripropylene glycol diacrylate, triethylene glycol dimethacrylate, tetraethylene glycol diacrylate, polyethylene glycol 200 diacrylate, tetraethylene glycol dimethacrylate, polyethylene glycol dimethacrylate, ethoxylated bisphenol A diacrylate, ethoxylated bisphenol A dimethacrylate, polyethylene glycol 600 dimethacrylate, poly(butanediol) diacrylate, pentaerythritol triacrylate, trimethylolpropane triethoxy triacrylate, glyceryl propoxy triacrylate, pentaerythritol tetraacrylate, pentaerythritol tetramethacrylate, dipentaerythritol monohydroxypentaacrylate, divinyl silane, trivinyl silane, dimethyl divinyl silane, divinyl methyl silane, methyl trivinyl silane, diphenyl divinyl silane, divinyl phenyl silane, trivinyl phenyl silane, divinyl methyl phenyl silane, tetravinyl silane, dimethyl vinyl disiloxane, poly(methyl vinyl siloxane), poly(vinyl hydro siloxane), poly (phenyl vinyl siloxane) and mixtures thereof.

Multi-ethylenically unsaturated monomers that are also neutralizable can also be used to prepare the PNPs. In such embodiments, these monomers are classified for the purposes of the present invention as both a multi-ethylenically unsaturated monomer and a neutralizable monomer.

Typically, unless specified otherwise, the amount of the at least one polymerized neutralizable ethylenically-unsaturated monomer is at least 0.5% by weight, based on the weight of the PNPs. Up to and including 100% polymerized neutralizable ethylenically-unsaturated monomer, based on the weight of the PNPs, can be effectively used in the particles of the present invention. It is preferred that the amount of polymerized ethylenically-unsaturated neutralizable monomer based on the weight of the PNPs is from 1% to 50%, more preferably from 3% to 40%, even more preferably from 5% to 25%, and most preferably from 10% to 20%.

Suitable neutralizable ethylenically-unsaturated monomers that can be incorporated as copolymerized units in the PNPs include, but are not limited to: acid-containing monomers, base-containing monomers, quaternizable monomers, and other functional monomers, in which the functionality can be subsequently formed into an acid or base functionality.

Suitable acid-containing monomers can have carboxylic acid functionality, which includes acrylic acid, methacrylic acid, crotonic acid, and acryloxypropionic acid. Acrylic acid and methacrylic acid are preferred based on cost and reactivity during polymerization. Suitable acid-containing monomers can have dicarboxylic acid functionality, which include itaconic acid, maleic acid, fumaric acid, citraconic acid. Suitable acid-containing monomers can have the half esters or half amides of dicarboxylic acids, such as containing one carboxylic acid functionality and one $C_{1-6}$ ester or one $C_{0-6}$ amide (e.g., acrylamide is a $C_0$ amide). Suitable acid-containing monomers can have sulfonic acid functionality, which include 2-acrylamido-2-methyl propane sulfonic acid, styrene sulfonic acid, vinyl sulfonic acid, sulfoethyl (meth)acrylate, and sulfopropyl (meth)acrylate. Suitable acid-containing monomers can have sulfinic acid functionality, which include 2-acrylamido-2-methyl propane sulfinic acid, styrene sulfinic acid, and vinyl sulfinic acid. Suitable acid-containing monomers can have phosphoric acid functionality, which includes 2-phosphoethyl (meth) acrylate and vinyl phosphoric acid. Phosphoric acid monomers are desirable as they can provide improved adhesion to certain substrates (e.g., metal). Suitable acid-containing monomers can have phosphinic acid functionality, such as vinyl phosphinic acid. Suitable acid-containing monomers can also have phenolic functionality, such as hydroxy styrene and derivatives thereof.

Suitable base-containing monomers can have amine functionality, which includes N,N-dimethylaminoethyl (meth)acrylate; N,N-diethylaminoethyl (meth)acrylate; N-t-butylaminoethyl (meth)acrylate; N,N-dimethylaminopropyl (meth)acrylamide; p-aminostyrene; N,N-cyclohexylallylamine; allylamine; diallylamine; dimethylallylamine; N-ethyldimethylallylamine; crotyl amines; and N-ethylmethallylamine. Suitable base-containing monomers can have pyridine functionality, which includes 2-vinylpyridine and 4-vinylpyridine. Suitable base-containing monomers can also have piperidine functionality, such as vinylpiperidines. Suitable base-containing monomers can also have imidazole functionality, which includes vinyl imidazole. Suitable base-containing monomers also include oxazolidinylethyl (meth)acrylate, vinylbenzylamines, vinylphenylamines, substituted diallylamines, 2-morpholinoethyl (meth)acrylate, acrylamide, methacrylamide, N-substituted (meth)acrylamides, methacrylamidopropyl trimethyl ammonium chloride (MAPTAC), diallyl dimethyl ammonium chloride (DADMAC), 2-trimethyl ammonium ethyl methacrylic chloride (TMAEMC), quaternary amine salts of substituted (meth)acrylic and (meth)acrylamido monomers, and the like.

Suitable functional monomers, in which the functionality can be subsequently formed into an acid or base include monomers containing: an epoxide functionality, such as glycidyl (meth)acrylate and allyl glycidyl ether; an anhydride, such as maleic anhydride; and a halide. Suitable halide-containing functional monomers include vinylaromatic halides and halo-alkyl(meth)acrylates. Suitable vinylaromatic halides include vinylbenzyl chloride, vinylbenzyl bromide, allyl chloride, and allyl bromide. Suitable haloalkyl(meth)acrylates include chloromethyl (meth)acrylate.

Typically, the alkyl (meth)acrylates useful in the present invention are ($C_1$-$C_{24}$) alkyl (meth)acrylates. Suitable alkyl (meth)acrylates include, but are not limited to, "low cut" alkyl (meth)acrylates, "mid cut" alkyl (meth)acrylates and "high cut" alkyl (meth)acrylates.

"Low cut" alkyl (meth)acrylates are typically those where the alkyl group contains from 1 to 6 carbon atoms. Suitable low cut alkyl (meth)acrylates include, but are not limited to: methyl methacrylate ("MMA"), methyl acrylate, ethyl acrylate, propyl methacrylate, butyl methacrylate ("BMA"), butyl acrylate ("BA"), isobutyl methacrylate ("IBMA"), hexyl methacrylate, cyclohexyl methacrylate, cyclohexyl acrylate and mixtures thereof.

"Mid cut" alkyl (meth)acrylates are typically those where the alkyl group contains from 7 to 15 carbon atoms. Suitable mid cut alkyl (meth)acrylates include, but are not limited to: 2-ethylhexyl acrylate ("EHA"), 2-ethylhexyl methacrylate, octyl methacrylate, decyl methacrylate, isodecyl methacrylate ("IDMA", based on branched ($C_{10}$)alkyl isomer mixture), undecyl methacrylate, dodecyl methacrylate (also known as lauryl methacrylate), tridecyl methacrylate, tetradecyl methacrylate (also known as myristyl methacrylate), pentadecyl methacrylate and mixtures thereof. Useful mixtures include dodecyl-pentadecyl methacrylate ("DPMA"), a mixture of linear and branched isomers of dodecyl, tridecyl, tetradecyl and pentadecyl methacrylates; and lauryl-myristyl methacrylate ("LMA").

"High cut" alkyl (meth)acrylates are typically those where the alkyl group contains from 16 to 24 carbon atoms. Suitable high cut alkyl (meth)acrylates include, but are not limited to: hexadecyl methacrylate, heptadecyl methacrylate, octadecyl methacrylate, nonadecyl methacrylate, cosyl methacrylate, eicosyl methacrylate and mixtures thereof. Useful mixtures of high cut alkyl (meth)acrylates include, but are not limited to: cetyl-eicosyl methacrylate ("CEMA"), which is a mixture of hexadecyl, octadecyl, cosyl and eicosyl methacrylate; and cetyl-stearyl methacrylate ("SMA"), which is a mixture of hexadecyl and octadecyl methacrylate.

The mid-cut and high-cut alkyl (meth)acrylate monomers described above are generally prepared by standard esterification procedures using technical grades of long chain aliphatic alcohols, and these commercially available alcohols are mixtures of alcohols of varying chain lengths containing between 10 and 15 or 16 and 20 carbon atoms in the alkyl group. Examples of these alcohols are the various Ziegler catalyzed ALOFL alcohols from Vista Chemical (now Sasol) company, i.e., ALOFL 1618 and ALOFL 1620, Ziegler catalyzed various Neodol alcohols from Shell Chemical Company, i.e. NEODOL 25L, and naturally derived alcohols such as. Proctor & Gamble's TA-1618 and CO-1270. Consequently, for the purposes of this invention, alkyl (meth)acrylate is intended to include not only the individual alkyl (meth)acrylate product named, but also to include mixtures of the alkyl (meth)acrylates with a predominant amount of the particular alkyl (meth)acrylate named.

The alkyl (meth)acrylate monomers useful in the present invention can be a single monomer or a mixture of monomers having different numbers of carbon atoms in the alkyl portion.

The (meth)acrylamide and alkyl (meth)acrylate monomers useful in the present invention can optionally be substituted. Suitable optionally substituted (meth)acrylamide and alkyl (meth)acrylate monomers include, but are not limited to: hydroxy ($C_2$-$C_6$)alkyl (meth)acrylates, dialkylamino($C_2$-$C_6$)-alkyl (meth)acrylates, dialkylamino ($C_2$-$C_6$)alkyl (meth)acrylamides.

Useful substituted alkyl (meth)acrylate monomers are those with one or more hydroxyl groups in the alkyl radical, especially those where the hydroxyl group is found at the β-position (2-position) in the alkyl radical. Hydroxyalkyl (meth)acrylate monomers in which the substituted alkyl group is a ($C_2$-$C_6$)alkyl, branched or unbranched, are preferred. Suitable hydroxyalkyl (meth)acrylate monomers include, but are not limited to: 2-hydroxyethyl methacrylate ("HEMA"), 2-hydroxyethyl acrylate ("HEA"), 2-hydroxypropyl methacrylate, 1-methyl-2-hydroxyethyl methacrylate, 2-hydroxypropyl acrylate, 1-methyl-2-hydroxyethyl acrylate, 2-hydroxybutyl methacrylate, 2-hydroxybutyl acrylate and mixtures thereof. The preferred hydroxyalkyl (meth)acrylate monomers are HEMA, 1-methyl-2-hydroxyethyl methacrylate, 2-hydroxypropyl methacrylate and mixtures thereof. A mixture of the latter two monomers is commonly referred to as "hydroxypropyl methacrylate" or "HPMA."

Other substituted (meth)acrylate and (meth)acrylamide monomers useful in the present invention are those with a dialkylamino group or dialkylaminoalkyl group in the alkyl radical. Examples of such substituted (meth)acrylates and (meth)acrylamides include, but are not limited to: dimethylaminoethyl methacrylate, dimethylaminoethyl acrylate, N,N-dimethylaminoethyl methacrylamide, N,N-dimethylaminopropyl methacrylamide, N,N-dimethylaminobutyl methacrylamide, N,N-di-ethylaminoethyl methacrylamide, N,N-diethylaminopropyl methacrylamide, N,N-diethylaminobutyl methacrylamide, N-(1,1-dimethyl-3-oxobutyl) acrylamide, N-(1,3-diphenyl-1-ethyl-3-oxobutyl) acrylamide, N-(1-methyl-1-phenyl-3-oxobutyl) methacrylamide, and 2-hydroxyethyl acrylamide, N-methacrylamide of aminoethyl ethylene urea, N-methacryloxy ethyl morpholine, N-maleimide of dimethylaminopropylamine and mixtures thereof.

Other substituted (meth)acrylate monomers useful in the present invention are silicon-containing monomers such as γ-propyl tri($C_1$-$C_6$)alkoxysilyl (meth)acrylate, γ-propyl tri ($C_1$-$C_6$)alkylsilyl (meth)acrylate, γ-propyl di($C_1$-$C_6$)alkoxy ($C_1$-$C_6$)alkylsilyl (meth)acrylate, γ-propyl di($C_1$-$C_6$)alkyl ($C_1$-$C_6$)alkoxysilyl (meth)acrylate, vinyl tri($C_1$-$C_6$) alkoxysilyl (meth)acrylate, vinyl di($C_1$-$C_6$)alkoxy($C_1$-$C_6$) alkylsilyl (meth)acrylate, vinyl ($C_1$-$C_6$)alkoxydi($C_1$-$C_6$) alkylsilyl (meth)acrylate, vinyl tri($C_1$-$C_6$)alkylsilyl (meth) acrylate, and mixtures thereof.

Vinylaromatic monomers are also useful as unsaturated monomers in the present invention, which include: styrene ("STY"), α-methylstyrene, vinyltoluene, p-methylstyrene, ethylvinylbenzene, vinylnaphthalene, vinylxylenes, and mixtures thereof. Useful vinylaromatic monomers also include their corresponding substituted counterparts, such as halogenated derivatives, i.e., containing one or more halogen groups, such as fluorine, chlorine or bromine; and nitro, cyano, ($C_1$-$C_{10}$)alkoxy, halo($C_1$-$C_{10}$)alkyl, carb($C_1$-$C_{10}$) alkoxy, carboxy, amino, ($C_1$-$C_{10}$)alkylamino derivatives and the like.

The nitrogen-containing compounds useful in the present invention include, but are not limited to: vinylpyridines such as 2-vinylpyridine or 4-vinylpyridine; lower alkyl ($C_1$-$C_8$) substituted N-vinyl pyridines such as 2-methyl-5-vinyl-pyridine, 2-ethyl-5-vinylpyridine, 3-methyl-5-vinylpyridine, 2,3-dimethyl-5-vinyl-pyridine, and 2-methyl-3-ethyl-5-vinylpyridine; methyl-substituted quinolines and isoquinolines; N-vinylcaprolactam; N-vinylbutyrolactam; N-vinylpyrrolidone; vinyl imidazole; N-vinyl carbazole; N-vinyl-succinimide; (meth)acrylonitrile; o-, m-, or p-aminostyrene; maleimide; N-vinyl-oxazolidone; N,N-dimethyl aminoethyl-vinyl-ether; ethyl-2-cyano acrylate; vinyl acetonitrile; N-vinylphthalimide; N-vinyl-pyrrolidones such as N-vinyl-thio-pyrrolidone, 3 methyl-1-vinyl-pyrrolidone, 4-methyl-1-vinyl-pyrrolidone, 5-methyl-1-vinyl-pyrrolidone, 3-ethyl-1-vinyl-pyrrolidone, 3-butyl-1-vinyl-pyrrolidone, 3,3-dimethyl-1-vinyl-pyrrolidone, 4,5-dimethyl-1-vinyl-pyrrolidone, 5,5-dimethyl-1-vinyl-pyrrolidone, 3,3,5-trimethyl-1-vinyl-pyrrolidone, 4-ethyl-1-vinyl-pyrrolidone, 5-methyl-5-ethyl-1-vinyl-pyrrolidone and 3,4,5-trimethyl-1-vinyl-pyrrolidone; vinyl pyrroles; vinyl anilines; vinyl versatates; and vinyl piperidines.

The substituted ethylenically unsaturated monomers useful in the present invention include, but are not limited to: allylic monomers, vinyl acetate, vinyl formamide, vinyl chloride, vinyl fluoride, vinyl bromide, vinylidene chloride, vinylidene fluoride and vinylidene bromide.

Other ethylenically-unsaturated monomers can also be incorporated as copolymerized units in the PNPs. Suitable ethylenically-unsaturated monomers include, but are not limited to: alkyl (meth)acrylates, vinyl acetates, alkenyl (meth)acrylates, aromatic (meth)acrylates, vinyl aromatic monomers, alkyl dienes such as butadiene and isoprene, nitrogen-containing compounds and their thio-analogs, and substituted ethylene monomers. (Meth)acrylic and (meth) acrylamide monomers are preferred for their reactivity during polymerization.

The PNP dispersions used in the present invention can be prepared by solution polymerization. By "solution polymerization" herein is meant free radical addition polymerization in a solvent for the polymer. By "solvent for the polymer" herein is meant that linear random (co)-polymers having substantially similar polymerized monomer units to the PNPs, are soluble in the solvent. A suitable solvent or mixture of solvents can also be selected using solubility parameter analysis as disclosed herein.

The PNPs can be prepared in a solvent, such as an organic solvent. Examples of organic solvents include, but are not limited to: hydrocarbons, such as alkanes, halohydrocarbons, such as chlorinated, fluorinated, and brominated hydrocarbons, aromatic hydrocarbons such as, ethers, ketones, esters, alcohols and mixtures thereof. Particularly suitable solvents include dodecane, mesitylene, xylenes, diphenyl ether, gamma-butyrolactone, ethyl acetate, ethyl lactate, propyleneglycol monomethyl ether acetate, caprolactone, 2-heptanone, methylisobutyl ketone, diisobutylketone, propyleneglycol monomethyl ether, and alkyl-alcohols, such as decanol, t-butanol, and isopropanol ("IPA").

The PNPs can be prepared by first charging a solvent heel or, alternatively, a mixture of solvent and some portion of the monomer(s) to a reaction vessel equipped with a stirrer, a thermometer and a reflux condenser. The monomer charge is typically composed of monomer(s), initiator and chain transfer agent, as appropriate. The solvent or solvent/monomer heel charge is heated with stirring under a nitrogen blanket. Typically, initiation temperatures are in the range of from 55° C. to about 125° C., although lower or higher initiator temperatures are possible using suitable low temperature or high temperature initiators known in the art. After the heel charge has reached a temperature sufficient to initiate polymerization, the monomer charge or balance of the monomer charge is added to the reaction vessel. The monomer charge time period is typically in the range of from 15 minutes to 4 hours, although both shorter and longer time periods are practicably envisioned. During monomer charge, the reaction temperature is typically kept constant, although it is possible to vary the reaction temperature. After completing the monomer mixture addition, additional initiator in solvent can be charged to the reaction and/or hold periods can be employed.

Suitable copolymerizable monomer combinations PNPs include, for example: HEMA/DEGDMA, MMA/DEGDMA/MAA, MMA/MAPS/DEGDMA/AA, MMA/MAPS/PETTA/MAA, MMA/MAPS/PPG4000DMA/AA, MMA/MAPS/DPEPA/MAA, MAPS/DEGDMA/AA, BA/DEGDMA/MAA, MMA/MAPS/TMPTMA/MAA, MMA/MAPS/DVB/AA, STY/MAPS/DVB/MAA, BA/MAPS/DVB/AA, BA/TMSMA/DVB/MAA, BA/MOPTSOMS/DVB/AA, BA/MOPMDMOS/DVB/MAA, BA/MAPS/TAT, ALMA/BA/DVB/AA, IBOMA/MAPS/DVB/MAA, IBOA/MAPS/DVB/AA, BA/DVB/MAA, BA/PGDMA/AA, BA/ALMA/MAA, BA/TMPTMA/AA, BA/DPEPA/MAA, EHA/DVB/MAA, EHA/ALMA/AA, EHA/TMPTMA/AA, EHA/DPEPA/ MAA, STY/DVB/MAA, STY/ALMA/MAA, EHA/STY/ALMA/MAA, MMA/BA/ALMA/MAA, STY/MMA/DVB/AA, MMA/butadiene/STY/AA, MMA/EA/ALMA/MAA, BA/ALMA/MATS/AA, STY/MATS/DVB/MAA, MMA/BA/MATS/AA, STY/MMA/MATS/DVB/MAA, MMA/BA/MATS/ALMA/MAA, BzA/TMPTMA/MAA, BzA/DVB/MAA, IDMA/BzMA/AA, MMA/ALMA/MATS/MAA, MMA/AA/TMPTA, and BA/MMA/AA/TMPTA.

Control of particle size and distribution can be achieved by such methods as choice of solvent, choice of initiator, total solids level, initiator level, type and amount of multifunctional monomer, type and amount of chain transfer agent, and reaction conditions. Particle sizes (mean particle diameter) can be determined using standard dynamic light scattering techniques, wherein the correlation functions can be converted to hydrodynamic sizes using LaPlace inversion methods, such as CONTIN.

Initiators useful in the free radical polymerization of the present invention include, for example, one or more of: peroxyesters, dialkylperoxides, alkylhydroperoxides, persulfates, azoinitiators, redox initiators and the like. Useful free radical initiators include, but are not limited to: benzoyl peroxide, t-butyl peroctoate, t-amyl peroxypivalate, cumene hydroperoxide, and azo compounds such as azoisobutylnitrile and 2,2'-azobis (2-methylbutanenitrile). It is preferred that the free radical initiator is t-amyl peroxypivalate. The amount of the free radical initiator used is typically from 0.05 to 10% by weight, based on the weight of total monomer.

Chain transfer reagents can optionally be used to prepare the PNPs useful in the present invention. Suitable chain transfer agents include, for example: alkyl mercaptans such as dodecyl mercaptan, aromatic hydrocarbons with activated hydrogens such as toluene, and alkyl halides such as bromotrichloroethane.

The PNPs of the present invention typically have an "apparent weight average molecular weight" in the range of 5,000 to 1,000,000, preferably in the range of 10,000 to 500,000 and more preferably in the range of 15,000 to 100,000. As used herein, "apparent weight average molecular weight" reflects the size of the PNP particles. The GPC elution times of the PNPs thereby provide an indication of an apparent weight average molecular weight measurement, and not necessarily an absolute weight average molecular weight measurement.

The solubility of the PNPs with the solvent is typically determined by matching their solubility parameters, such as the Van Krevelen parameters of delta d, delta p, delta h and delta v. See, for example, Van Krevelen et al., *Properties of Polymers. Their Estimation and Correlation with Chemical Structure*, Elsevier Scientific Publishing Co., 1976; Olabisi et al., *Polymer-Polymer Miscibility*, Academic Press, NY, 1979; Coleman et al., *Specific Interactions and the Miscibility of Polymer Blends*, Technomic, 1991; and A. F. M. Barton, *CRC Handbook of Solubility Parameters and Other Cohesion Parameters*, $2^{nd}$ Ed., CRC Press, 1991. Delta d is a measure of dispersive interactions, delta p is a measure of polar interactions, delta h is a measure of hydrogen bonding interactions, and delta v is a measure of both dispersive and polar interactions. Such solubility parameters can either be calculated, such as by the group contribution method, or determined by measuring the cloud point of a polymeric material in a mixed solvent system consisting of a soluble solvent and an insoluble solvent. The solubility parameter at the cloud point is based on the weighted percentage of the solvents. Typically, a number of cloud points are measured for the material and the central area defined by such cloud points is defined as the area (range) of solubility parameters of the material.

In the method of preparing an aqueous PNP dispersion according to one embodiment of the present invention, a PNP dispersion is prepared containing the PNPs as described earlier and at least one water-compatible solvent. Suitable weight percentages of the PNPs in the aqueous PNP dispersion, based on total weight of the aqueous PNP dispersion, is typically from 1 wt. % to 90 wt. %, more typically from 2 wt. % to 75 wt. %, even more typically from 4 wt. % to 65 wt. %, further more typically from 8 wt. % to 55 wt. %, and most typically from 10 wt. % to 45 wt. %.

Suitable water-compatible solvents are at least partially soluble in water at process conditions. Typically, suitable water-compatible solvents are at least 10 wt. %, more typically at least 15 wt. %, even more typically at least 20 wt. %, even further more typically at least 30 wt. %, further typically at least 50 wt. %, even further typically at least 75 wt. %, and most typically completely soluble in water at process conditions. Suitable water-compatible solvents are listed in *Lange's Handbook of Chemistry*, which include halohydrocarbons, such as chlorinated, fluorinated, and brominated hydrocarbons, ethers, ketones, esters, alcohols and mixtures thereof. Particularly suitable solvents include diphenyl ether, gamma-butyrolactone, ethyl acetate, ethyl lactate, propyleneglycol monomethyl ether acetate, caprolactone, 2-heptanone, methylisobutyl ketone, diisobutylketone, methylethylketone ("MEK"), propyleneglycol monomethyl ether, and alkyl-alcohols, such as decanol, preferably the C1-C5 alkyl alcohols such as t-butanol and isopropanol ("IPA").

Suitable solvents will also form azeotropes (binary and higher order azeotropes) with water at process conditions. Solvents that form azeotropes with water are defined wherein the concentration of solvent in the vapor phase of a mixture of water and the solvent at equilibrium at the process conditions is at least 10 wt. %, typically at least 20 wt. %, more typically at least 30 wt. %, even more typically at least 40 wt. %, and preferably at least 50 wt. %. Suitable solvents that also form azeotropes with water are provided in *Lange's Handbook of Chemistry*. Such solvents preferably include water-compatible solvents which form good azeotropes with water, such as C1-C4 di(alkyl)(di)ethylene glycol, C1-C3 alcohols such as IPA, acetone, and MEK.

While the preparation of the PNP dispersions of the present invention does not require the use of surfactants, and it is typical that the PNP dispersions of the present invention are substantially free of surfactants, surfactants may be included. When present, the amount of surfactants is typically less than 3 weight percent, more typically less than 2 weight percent, even more typically less than 1 weight percent, further typically less than 0.5 weight percent, and even further typically less than 0.2 weight percent, based on total weight of the PNPs.

The water-compatible solvent can be provided to the PNP dispersion in a variety of ways. One way is to carry out the solvent-based free radical polymerization of the PNPs in non-water-compatible solvent, the dispersion of which is subsequently diluted with a water-compatible solvent. In this case, the water-compatible solvent is compatible with the non-water-compatible solvent. In addition, at least a portion of the non-water-compatible solvents of PNP dispersions can be removed, such as by vacuum distillation, prior to diluting with a water-compatible solvent. When a substantial fraction of the non-water-compatible solvent is removed, certain PNPs that are characteristically hard (e.g., having a Tg greater than the processing temperature, or which are highly crosslinked) can be dried to a powder and subsequently dispersed in a water-compatible solvent, an aqueous water-containing solvent, or even water. A preferred way is to carry out the solvent-based free radical polymerization of the PNPs in a water-compatible solvent. In this case, the water-compatible solvent may also be a mixture of at least two different solvents, the mixture of which is water compatible.

In the method of preparing an aqueous PNP dispersion according to the present invention, at least a portion of the neutralizable polymerized units of the PNPs are neutralized with at least one neutralizing agent to form an at least partially neutralized PNP dispersion. The neutralizable polymerized units of the PNPs can be neutralized in a variety of ways. When the neutralizable polymerized units are acidic, the neutralizing agent will typically be basic. Likewise, when the neutralizable polymerized units are basic, the neutralizing agent will typically be acidic.

Suitable basic neutralizing agents include inorganic and organic bases. Suitable inorganic bases include the variety of the hydroxide, carbonate, bicarbonate, acetate bases of the Group I [Li, Na, K, Rb, Cs] and Group II [Be, Mg, Ca, Sr, Ba] elements. Suitable organic bases include ammonia, primary/secondary/tertiary amines, diamines, and triamines. Preferred basic neutralizing agents include sodium hydroxide (NaOH), ammonium hydroxide ($NH_4OH$), and ammonia. When used in aqueous-based coating formulations, ammonia is preferred as a neutralizing base as it readily evaporates from the coating film, thus reducing sensitivity of the dried coating to water.

Suitable acidic neutralizing agents include, but are not limited to: carboxylic acids, such as formic, acetic, propanoic, chloroacetic, and trichloroacetic acid; dicarboxylic acids, such as maleic, fumaric, malonic, and oxalic acid; (di)carboxylic/hydroxyl acids, such as glycolic, lactic, malic, and tartaric acid; aromatic acids, such as benzoic, mandelic, phthalic, and salicylic acid; and a variety of other acids, such as boric, carbonic, citric, iodic, nitrous, nitric, periodic, phosphoric, phosphorous, sulfuric, sulfurous, and hydrochloric acid.

Neutralization can also be carried out by including a quaternizable ethylenically unsaturated monomer in the PNP polymerization, and subsequently quaternizing the PNPs, as described in U.S. Pat. No. 5,212,251. For example, amine functional monomers are suitable quaternizable ethylenically unsaturated monomers, for which suitable compounds capable of quaternizing amine functional monomers include those selected from the group consisting of alkyl halides, aryl halides, epichlorohydrin and epoxides such as, for example, ethylene oxide, propylene oxide, epoxy derivatives of Bisphenol A, and the like. Quaternizing agents capable of quaternizing quaternizable monomers generally include any alkylating agents that will react preferentially with the quaternizable (e.g., amine) functionality.

In certain embodiments of the present invention, the neutralizable polymerized units are provided by copolymerized reactive functional groups. Such groups can be post-reacted with a reactant containing a basic, or acidic functionality, prior to neutralization of the basic, or acidic, functionality. Suitable reactants contain both a nucleophile and basic, or acidic, functionality. Typical reactants contain an amine or mercaptan nucleophile. Preferred reactants contain an amine or mercaptan nucleophile and one or more carboxylic acid functionalities, such as at least one of the following: mercapto acids: e.g., $HS—(CH_2)_n—COOH$, n=1-3; and amino acids: e.g., glycine, alanine, leucine, aspartic acid, glutamic acid. For reasons of cost and avoiding the generation of halide (e.g., chloride and bromide) ions, which tend to be detrimental to metal, both epoxide and anhydride polymerizable functionality are preferred to halide. Amino acids are typically preferred over mercapto acids as post-reactants, due to cost, availability and odor concerns associated with the mercaptan functionality. Neutralization of the basic or acidic functionality of the post-reacted reactants is carried out with the suitable neutralizing agents as described above to provide an at least partially neutralized PNP dispersion.

The amount of neutralizing agent to neutralize the PNP dispersion is typically determined on a molar basis of neutralizing agent to neutralizable polymerized units of the PNPs. Without being bound to a particular theory, the amount of neutralizable polymerized units (i.e., level of charge) needed to stabilize the PNPs (i.e., maintain particle size during conversion from non-aqueous to aqueous medium) will vary as PNP composition and properties are varied. It is believed that the PNP hydrophobicity, Tg, crosslinking level, and type of counterion from the neutralizing agent are important variables. For providing stabilized aqueous PNP dispersions (i.e., flocculation of the PNPs is preferably minimized), the neutralizable polymerized units are preferably at least 20%, more preferably at least 50%, even more preferably at least 80%, and most preferably at least 90% neutralized. The neutralizing agent may be added in excess of that which is needed to completely neutralize the PNP dispersion (i.e., over-neutralization), however this is typically undesirable as excess neutralization agent can degrade properties (e.g., increase odor) of the PNP dispersions. In such cases, the amount of neutralization agent is typically no more than 120%, and more typically no more than 110% of that which is necessary to completely neutralize the PNPs.

Neutralizing the PNPs can be carried out in a variety of ways. In one embodiment, the PNP dispersion can be added to a solution containing the neutralizing agent while stirring. Preferably, the neutralizing agent is added as an aqueous solution over time while stirring the PNP dispersion to provide an at least partially neutralized PNP dispersion.

In the method of preparing an aqueous PNP dispersion according to the present invention, the at least partially neutralized PNP dispersion is combined with an aqueous medium. The aqueous medium is any liquid medium containing water, and is preferably water. The aqueous medium may contain the neutralizing agent(s) for neutralizing the PNPs, in which case the PNP dispersion can be simultaneously neutralized and combined with an aqueous medium. The aqueous medium may also contain surfactants, which can alter the stability of the PNPs, or alter other properties of the PNP dispersion, such as its surface tension.

Combining the PNP dispersion and an aqueous medium can be carried out using a variety of methods. In one embodiment, the at least partially neutralized PNP dispersion can be added to an aqueous medium. In another embodiment, an aqueous medium can be added to the PNP dispersion. In another embodiment, the at least partially PNP dispersion and the aqueous medium can be combined simultaneously, such as in a mixing head. Various methods and equipment which can be used for mixing are described in *The Chemical Engineer's Handbook, 5th Edition*, Perry and Chilton, Eds., McGraw-Hill, Ch. 21, 1973. Typically, the aqueous phase is continuously stirred while adding the PNP dispersion to it to ensure that the solvent is intimately mixed with the aqueous medium, which minimizes flocculation of the PNPs.

Additional embodiments of the present invention whereby the PNPs are prepared in solvent, neutralized, stripped of solvent, and diluted with an aqueous medium (e.g., water) are possible, as follows:

In one embodiment of the present invention, PNPs are prepared in a water-miscible solvent, such as IPA, neutralized with a neutralizing agent to form either a single or higher-order phase solution of neutralized PNPs, and diluted with an aqueous medium to from an aqueous PNP dispersion. By "higher-order phase solution" is meant a composition having at least two thermodynamically distinct phases, which contains PNPs and solvent. The aqueous PNP dispersion may subsequently be stripped of solvent.

In one embodiment of the present invention, PNPs are prepared in a water-compatible solvent, such as MEK, neutralized with a neutralizing agent to form either a single or higher-order phase solution of neutralized PNPs, and diluted with an aqueous medium to from an aqueous PNP dispersion. The aqueous PNP dispersion of this embodiment may subsequently be stripped of solvent, the PNPs may be extracted from the dispersion, or the solvent may be extracted from the dispersion. A combination of stripping and extraction processes can also be used for reducing the solvent content of the aqueous PNP dispersion of this embodiment.

In one embodiment of the present invention, PNPs are prepared in a water-immiscible solvent, such as toluene, then neutralized with a neutralizing agent to form either a single or higher-order phase solution of neutralized PNPs, and then diluted with an aqueous medium to from an aqueous PNP dispersion. The aqueous PNP dispersion of this embodiment may subsequently be stripped of solvent, the PNPs may be extracted from the dispersion, or the solvent may be extracted from the dispersion. A combination of stripping and extraction processes can also be used for reducing the solvent content of the aqueous PNP dispersion of this embodiment.

In one embodiment of the present invention, PNPs are first prepared in a solvent, then the solvent is removed, such as by stripping, then the PNPs are neutralized with a neutralizing agent and diluted with an aqueous medium to from an aqueous PNP dispersion.

In one embodiment of the present invention, PNPs are first prepared in a solvent, then the PNPs are neutralized with a neutralizing agent, then the solvent is removed, such as by stripping, and then the PNPs are diluted with an aqueous medium to form an aqueous PNP dispersion.

The weight ratio of the at least partially neutralized PNP dispersion to the aqueous medium is typically in the range of from 0.1:100 to 100:1, more typically in the range of from 1:100 to 10:1, even more typically in the range of from 1:20 to 2:1, and further typically in the range of from 1:5 to 1:1. When the water-compatible solvent is completely miscible in water, there is no limit to this ratio to provide an aqueous PNP dispersion, having one liquid phase. When the water-compatible solvent is partially soluble in water, then this ratio is typically limited to the solubility of the solvent in water at the process conditions, to provide a single liquid phase aqueous PNP dispersion.

In certain embodiments of the present invention, it is desirable to remove at least a portion of the solvent from the aqueous PNP dispersion, thereby enriching the aqueous and PNP fractions of the dispersion. In these embodiments, preferably at least 25 wt. %, more preferably at least 50 wt. %, even more preferably at least 75 wt. %, and most preferably substantially all of the solvent is exchanged with water. Removal of the solvent is preferably carried out under conditions that minimize destabilization (i.e., flocculation) of the PNPs. Various methods to remove solvents from water-solvent mixtures can be used in the present invention, many of which are described in *The Chemical Engineer's Handbook*, 5th Edition, Perry and Chilton, Eds., McGraw-Hill, Ch. 13, "Distillation", 1973. Preferably, azeotropic distillation methods are used for removing at least a portion of solvent. See Id., pp. 13-38, et seq. Examples of suitable azeotropic binary water-solvent pairs are provided in Id., Table 13-10. Preferably, the azeotropic mixture, whether binary or higher order, contains a single liquid phase during azeotropic distillation (i.e., homogeneous azeotropic distillation).

In one embodiment of the present invention, it is desirable to prepare aqueous PNP dispersions that do not require a neutralizing agent to impart particle stability. In this embodiment, a dispersion of PNPs can be prepared in a solvent that is both a "good solvent" for the PNPs and compatible or miscible in water. Good solvents for the PNPs will typically swell the PNPs. Good solvents for the PNPs are also defined wherein the solubility parameters of the good solvent and the PNPs are substantially matched. Solvents that are compatible or miscible with water are described herein. Examples of such good solvents for acrylic-containing PNPs, which are also compatible or miscible with water, include isopropanol, alkyl cellosolves, (e.g., butyl cellosolve) and alkyl carbitols (e.g., ethyl carbitol). In this embodiment, the PNPs do not require the addition of neutralizing agents to impart particle stability when combined with water. The aqueous PNP dispersion of this embodiment can be prepared by combining the PNP solvent dispersion with an aqueous medium, such as water. In this embodiment, the weight percentage of water, based on the total weight of the aqueous PNP dispersion, is typically at least 1 wt. %, more typically at least 2 wt. %, even more typically at least 5 wt. %, further typically at least 10 wt. %, even further typically at least 25 wt. %, more further typically at least 50 wt. %, and most typically at least 75 wt. %.

The aqueous PNP dispersions of the present invention can have a wide range of PNP weight fractions. Typically, the PNP weight fractions will range from 0.1 wt. % to 99 wt. %, more typically from 1 wt. % to 90 wt. %, even more typically from 2 wt. % to 75 wt. %, further typically from 5 wt. % to 50 wt. %, and most typically 10 wt. % to 40 wt. %. Viscous, syrupy-like, aqueous PNP dispersions typically result when the PNP weight fraction is greater than 25 wt. %, while thin, liquid-like aqueous PNP dispersions are generally provided when the PNP weight fraction is less than 15 wt. %. These viscosity versus solid concentration guidelines will vary with composition and temperature.

The aqueous PNP dispersions of the present invention can be used as associative thickeners. In these embodiments, the PNPs further comprise an average of at least two phobes extending from the surface of the PNPs. The phobes can be suitably provided to the PNPs in various ways. One way is to include an average of two ethylenically unsaturated phobe-containing monomers in the synthesis of the PNPs. Suitable phobe-containing monomers can be any ethylenically unsaturated monomer that has a phobe. Suitable phobes are typically an alkyl group comprising at least four carbon atoms, more typically at least six carbon atoms, even more typically at least eight carbon atoms, and further typically at least 10 carbon atoms. The phobe-containing monomers are copolymerizable with the PNPs of the present invention, as described herein, have an ethylenically-unsaturated functionality. The phobe-containing monomers may optionally contain at least one water soluble spacer group, such as a 2-100 polyethyleneoxide (PEO) linkage, between the phobe and the ethylenically unsaturated functionality.

In a preferred embodiment, the phobe-containing monomers have a water-soluble spacer molecule (e.g., a polyethylene oxide spacer) between the phobe and the ethylenically unsaturated functionality. Suitable examples include methacrylated nonionic surfactants having C10-C30 ethoxylates, preferably C12-C18 ethoxylates.

In another embodiment, the phobes of the PNP associative thickeners can be provided by post-reacting phobe-containing reactants to PNPs containing polymerized units having chemical functionalities. PNPs having suitable chemical functionalities are provided above. Suitable phobe-containing reactants include amines, alcohols, and anhydrides.

Suitable phobe-containing monomers and reactants will typically have a water solubility (or weight average water solubility for mixtures) of less than 10, preferably less than 5, more preferably less than 2, and further preferably less than 1 weight percent at 25° C. By "water solubility" herein is meant, the solubility of the phobe-containing monomers and reactants in water.

The PNP associative thickeners and the PNP aqueous dispersions of the present invention can be used as a dispersion in the polymerization solvent, as an aqueous dispersion as provided herein, or as an isolate, for example, by vacuum evaporation, by precipitation into a non-solvent, and by spray drying. When isolated, PNPs can be subsequently redispersed in a medium appropriate for incorporation into a coating composition.

The PNP associative thickeners of the present invention can be incorporated in various aqueous-based compositions (e.g., coatings, adhesives, polishes, waxes, and various other organic and inorganic dispersions) by admixing the PNPs or a dispersion of the PNPs with the aqueous-based compositions. A variety of optional composition adjuvants, which are well known to those skilled in the art, can likewise be added. In coatings applications, the coating composition can include an aqueous or non-aqueous medium. The coating composition can contain conventional coating adjuvants such as, for example, tackifiers, pigments, emulsifiers, crosslinkers, monomers, oligomers, polymers, solvents, coalescing agents, buffers, neutralizers, humectants, wetting agents, biocides, plasticizers, antifoaming agents, colorants, waxes, anti-oxidants, and other thickeners or associative thickeners.

The coatings containing the PNP associative thickeners of the present invention can be applied by conventional application methods such as, for example, brush or paint roller, air-atomized spray, air-assisted spray, airless spray, high volume low pressure spray, air-assisted airless spray, curtain coating, roller coating, reverse roller coating, gravure coating, flexography, ink-jet, bubble-jet, and electrostatic spray.

The coating containing the PNP associative thickeners of the present invention can be applied to a substrate such as, for example, plastic including sheets and films, wood, metal, leather, woven or nonwoven fabric, hair, skin, nails, paper, previously painted surfaces, cementitious substrates, and asphaltic substrates.

EXAMPLES

Ex. 1

Aqueous PNP Dispersion: 70 MMA/10 TMPTA/20 MAA

A dispersion of methyl methacrylate/methacrylic acid/trimethylol propane triacrylate (70/20/10 wt. %) PNPs was prepared via solution polymerization in IPA as follows: A 5 liter reactor was fitted with a thermocouple, a temperature controller, a purge gas inlet, a water-cooled reflux condenser with purge gas outlet, a stirrer, and a monomer feed line. To a separate vessel was charged 450 grams of a monomer mixture (A) containing 315 g MMA, 90 g MAA, and 45 g TMPTA. To an additional vessel was charged an initiator mix (B) consisting of 18 g of a 75% solution of t-amyl peroxypivalate in mineral spirits (Triganox 125-C75), and 113 g isopropyl alcohol. A charge of 2330 g IPA was added to the reactor. After sweeping the reactor with nitrogen for approximately 30 minutes, heat was applied to bring the reactor charge to 79° C. When the contents of the reactor reached 79° C., a dual feed of both the monomer mixture (A) and the initiator mix (B) to the reactor. The two mixtures were fed uniformly using feed pumps over 120 minutes. At the end of the monomer and initiator feeds, the batch was held at 79° C. for 30 minutes before adding the first of three initiator chasers consisting of 9 g of a 75% solution of t-amyl peroxypivalate in mineral spirits (Triganox 125-C75), and 22.5 gm. IPA. A second initiator chaser addition was made 30 minutes after the first initiator chaser addition. Similarly, a final initiator chaser addition was made 30 minutes after the second initiator chaser addition. The batch was then held at the polymerization temperature of 79° C. for and additional 2½ hours to achieve full conversion of monomer.

At the end of the final hold, the polymerized MAA units of the PNPs were neutralized by addition to the PNP dispersion a mixture of 42.5 g of an aqueous 50% solution of $NH_4OH$ and 450 g water.

The neutralized PNP dispersion was transferred to a roto-evaporator and stripped of solvent at ca. 35° C. under full house vacuum. After removing substantially all of the solvent, the PNP dispersion was further diluted with water to ca. 40 wt. % PNP in water. Particle size was measured at ~5.0 nm. The resulting aqueous PNP dispersion can be used as a stabilizer for emulsion polymerizations, such as for use in preparing aqueous latex paints.

Ex. 2

PNPs in MEK, Neutralized and Stripped into Water

PNPs of butyl acrylate/methyl methacrylate/acrylic acid/allyl methacrylate (49.5/33/7.5/10 wt. %) were prepared via solution polymerization. A 1 liter reactor was fitted with a thermocouple, a temperature controller, a purge gas inlet, a water-cooled reflux condenser with purge gas outlet, a stirrer, and a monomer feed line. To a separate vessel was charged 150 g of a monomer mixture (A) consisting of 74.3 g butyl acrylate (BA), 49.5 g methyl methacrylate (MMA), 11.3 g acrylic acid (AA), and 15.0 g allyl methacrylate (ALMA). To an additional vessel was charged an initiator mix (B) consisting of 3.0 g of a 75% solution of t-amyl peroxypivalate in mineral spirits (Triganox 125-C75), and 37.5 g methyl ethyl ketone (MEK). A charge of 528 g MEK was added to the reactor. After sweeping the reactor with nitrogen for approximately 30 minutes, heat was applied to bring the reactor charge to 78° C. When the contents of the reactor reached 78° C., a dual feed of both the monomer mixture (A) and the initiator mix (B) to the reactor. The two mixtures were feed uniformly using feed pumps over 120 minutes. At the end of the monomer and initiator feeds, the batch was held at 78° C. for 30 minutes before adding the first of three initiator chasers consisting of 3.0 g of a 75% solution of t-amyl peroxypivalate in mineral spirits (Triganox 125-C75), and 7.50 g MEK. A second initiator chaser addition was made 30 minutes after the first initiator chaser addition. Similarly, the final initiator chaser addition was made 30 minutes after the second initiator chaser addition. The batch was then held at the polymerization temperature of 78° C. for and additional 2½ hours to achieve full conversion of monomer.

At the end of the final hold, the batch was neutralized with a mixture of 11.0 g of a 50% aqueous solution of $NH_4OH$ and 150 g water. The neutralized polymer solution was transferred to a roto-evaporator and stripped of solvent at ~45° C. under full house vacuum. After removing all solvent the batch was further diluted with water to ~30% polymer in water and pH adjusted to ~8.0. Particle size was measured at ~4.7 nm.

Ex. 3

PNPs Prepared in IPA, Dried and Redispersed into Water

PNPs of methyl methacrylate/acrylic acid/trimethylol propane triacrylate (75/20/5 wt. %) was prepared via solution polymerization at 20% solids in isopropyl alcohol as described in Example 1. Particle size was measured at 2.4 nm.

At the end of the final hold, a portion of the batch was charged to a 5 fold excess of heptane. The nanoparticle readily precipitated from the heptane solution, was filtered using a Buchner filter, and dried in a vacuum oven at ~60° C. at full house vacuum to remove all volatile material. To 100 g dried PNPs was added 300 g water and 20.5 g of a 50% aqueous $NH_4OH$ solution. The mixture was agitated for ~1 hour to achieve a clear homogeneous solution. Particle size was measured at 2.3 nm.

Ex. 4

PNPs Prepared in IPA, Neutralized, Dried and Redispersed into Water

Following the Example 3, at the end of the final hold, 100 g of the PNP dispersion was neutralized with 4.4 μm of a 50% aqueous solution of NaOH. The neutralized PNP dispersion was charged to a five-fold excess of heptane to precipitate the PNPs. The precipitated PNPs were isolated by filtration and dried to constant weight in a vacuum oven at ~60° C. The dried PNPs were then re-dispersed into water to provide a 30% solids solution. Particle size was 2.4 nm.

Ex. 5

Aqueous PNP Dispersions—Vary Neutralizable Unit Content

Three PNP dispersions were prepared at 20 wt. % solids in n-propanol solvent following the general methods of Example 1. The PNP compositions contained 10 wt. % TMPTA, between 3 wt. % and 7.5 wt. % of MAA, and the remainder of the monomer of equal amounts of BA and MMA. Mean particles sizes of the PNPs in n-propanol were between ca. 4 and 10 nm. The PNP dispersions were neutralized with a sufficient amount of basic neutralizing agent to neutralize substantially all of the MAA acid units. The PNP dispersions were then converted from n-propanol to an aqueous medium using azeotropic distillation methods. The particle size distributions of the resulting aqueous PNP dispersions are provided in the following table:

| Azeotrope Conditions | Neutraliz'n Agent | Particle Size Distribution of 10 wt. % Aqueous Dispersion | | |
|---|---|---|---|---|
| | | 3% wt. % MAA | 5% wt. % MAA | 7.5% wt. % MAA |
| ca. 100° C., ambient pressure | NaOH | — | 6.5 nm (65 vol %) 23 nm (35 vol %) | — |
| ca. 100° C., ambient pressure | NH$_4$OH | — | 50 nm (66 vol %) 146 nm (34 vol %) | — |
| Ca. 50° C., ca. 120 mm Hg | NaOH | 22 nm | 6.5 nm (98 vol %) 30 nm (2 vol %) | 4 nm |

The above examples show that the PNP particle stability increases with increasing charge, lower temperature during the azeotropic distillation, and that NaOH appears to be a better neutralization agent than NH$_4$OH.

Ex. 6

Use of Aqueous PNP Dispersion as Rheology Modifier

An aqueous PNP dispersion of the composition 25 BA/25 MMA/10 TMPTA/40 MAA, mean particle size of 5–10 nm is prepared according the general procedures of Example 1. The aqueous PNP dispersion can be used as a rheology modifier for water-based industrial and consumer products, such as latex-based coatings. In this example, 1 part by weight, based on solids, of the PNP dispersion is added to 100 parts, based on solids, of an aqueous acrylic semigloss coating composition. The sag time of the aqueous acrylic semigloss coating composition containing the PNPs is increased.

Ex. 7

PNP-Phobe Associative Thickeners

Phobe-containing Monomer:

A PNP-phobe associative thickener composition was prepared as follows. Phobe-containing monomer 30 C$_{18}$(EO)$_{92}$-IDI was prepared by reacting a nonionic surfactant of dodecyl/stearyl ethoxylate with 3-isopropenyl-α,α-dimethylbenzyl isocyanate (IDI), in the presence of dibutyltin dilaurate, in toluene at 90° C. for 1 hour—followed by evaporation of the solvent.

PNP Compositions:
PNP A: 26.5 BA/26.0 MMA/10.0 TMPTMA/30 C$_{18}$(EO)$_{92}$-IDI/7.5 MAA
PNP B: 11.5 BA/1.0 MMA/10.0 TMPTMA/60 C$_{12}$(EO)$_{92}$-IDI/7.5 MAA Aqueous PNP Dispersion To a flask containing 355 g of 1-propanol was added, at 82° C. under nitrogen, 100 g of monomer solution (in separate polymerizations each for the PNP A and PNP B compositions) over 1.5 hours, and a solution of 7.5 g of 75 wt. % t-amyl peroxypivalate in aliphatic hydrocarbons in 37.5 g 1-propanol over 4.5 hours. When the initiator feed was complete, the reaction was stirred an additional 30 minutes at 82° C. The heat was removed and 180 g of water was added over 10 minutes, followed by addition of a neutralization solution of 4.4 g of sodium hydroxide in 24.4 g of water. Clear dispersions of neutralized 14.3 wt. % PNP particles in solvent/water medium were formed. Propanol was exchanged with water via azeotropic distillation to generate 10 wt. % solids clear aqueous PNP dispersions, having particle size (mean diameter via light scatter) of 8.2 nm for PNP A and 6.6 nm for PNP B.

Associative Thickeners

The PNP A and PNP B aqueous dispersions were demonstrated to have utility as thickeners:
Thickener for water:
10 wt. % PNP A in water: viscosity>100,000 cps;
10 wt. % PNP B in water: viscosity=1,250 cps.
Viscosity measurements were carried out on a Brookfield Model DV-II Programmable Rheometer using spindle LV-4 at 12 rpm.

Use as associative thickener for polymer latex:

| | KU(cps)[a] | ICI(cps)[b] |
|---|---|---|
| Ref.: 100 gms Rhoplex ™ SG-10M acrylic latex[c] + 26.5 gm water | 45 | 0.05 |
| Ex. 100 gms Rhoplex ™ SG-10 M acrylic latex[c] + 25.9 gm water + 0.6 gm PNP B | 134 | 0.40 |

[a]KU = Stormer viscosity (10$^2$ sec$^{-1}$); measured on Brookfield model KU-1P
[b]ICI is "high shear viscosity" (10$^3$ sec$^{-1}$); measured on ICI Cone & Plate viscometer
[c]Rohm and Haas Company, Philadelphia, PA

The invention claimed is:
1. A method of preparing an aqueous polymeric nanoparticle (PNP) dispersion, comprising the steps of:
   preparing a PNP dispersion, said PNP dispersion comprising:
   (i) PNPs having a diameter in the range of from 1 to 8.2 nanometers, said PNPs comprising as polymerized units at least one multi-ethylenically-unsaturated monomer and at least one neutralizable ethylenically- unsaturated monomer and an ethylenically-unsaturated phobe-containing monomer containing a water soluble spacer group between said phobe and the ethylenic unsaturation such that there is an average of at least two phobes extending from the surface of said PNPs, each phobe having an alkyl group with at least four carbon atoms; and (ii) at least one solvent, wherein the solubility of the solvent in water at process conditions is at least 10 weight percent;

neutralizing at least a portion of the polymerized units formed from the at least one neutralizable ethylenically-unsaturated monomer with at least one neutralizing agent to form an at least partially neutralized PNP dispersion; and combining the at least partially neutralized PNP dispersion with an aqueous medium.

2. The method according to claim 1, wherein the weight percentage of the at least one neutralizable ethylenically-unsaturated monomer is at least 1 weight percent, said weight percentage being based on total weight of the PNPs.

3. The method according to claim 2, wherein the at least one neutralizable ethylenically-unsaturated monomer is selected from the group consisting of acrylic acid and methacrylic acid.

4. The method according to claim 1, wherein the weight percentage of the PNPs in the PNP dispersion of step (a), based on total weight of the PNP dispersion, is in the range of from 1 weight percent to 90 weight percent.

5. The method according to claim 1, wherein the step of a preparing a PNP dispersion comprises: polymerizing a mixture of monomers comprising the at least one multi-ethylenically-unsaturated monomer and the at least one neutralizable ethylenically-unsaturated monomer and the ethylenically-unsaturated phobe-containing monomer in a polymerization medium, said polymerization medium comprising at least one solvent; at least one free radical initiator, and less than 3 weight percent, based on total PNP weight, of a surfactant.

6. The method according to claim 1, further comprising the step of removing at least a portion of the at least one solvent.

7. An aqueous PNP dispersion, comprising:
(a) PNPs having a diameter in the range of from 1 to 8.2 nanometers, said PNPs comprising an average of at least two phobes extending from the surface of said PNPs, each phobe having an alkyl group with at least four carbon atoms and as polymerized units at least one multi-ethylenically-unsaturated monomer and an ethylenically-unsaturated phobe-containing monomer containing a water soluble spacer group between said phobe and the ethylenic unsaturation and at least one neutralizable ethylenically-unsaturated monomer selected from a group consisting of acid-containing monomers having at least one of sulfonic acid functionality, sulfinic acid functionality, phosphoric acid functionality, phosphinic acid functionality, and phenolic functionality; base-containg monomer having at least one of amine functionality, pyridine functionality, piperidine functionality, and imidazole functionality; oxazolidinylethyl (meth)acrylates, vinylbenzylamines, vinylphenylamines, substituted diallylamines, 2-morpholinoethyl (meth)acrylates, acrylamides, methacrylamides, N-substitutes (meth)acrylamides, methacrylamidopropyl trimethyl ammonium chlorides (MAPTAC), diallyl dimethyl ammonium chlorides (DADMAC), 2-trimethyl ammonium ethyl methacrylic chlorides (TMAEMC), quaternary amine salts of substituted (meth)acrylic and (meth)acrylamido monomers; and monomers having at least one of an ahydride, or an epoxide or halide functionality which can subsequently be converted to an acid or base functionality;

(b) at least one neutralizing agent to partially neutralize the at least one neutralizable ethylenically-unsaturated monomer;

(c) at least one solvent, wherein the solubility of the solvent in water at process conditions is at least 10 weight percent; and (d) an aqueous medium.

8. A PNP dispersion, comprising: PNPs having a diameter in the range of from 1 to 8.2 nanometers, said PNPs comprising as polymerized units at least one multi-ethylenically-unsaturated monomer and at least one neutralizable ethylenically-unsaturated monomer and an ethylenically-unsaturated phobe-containing monomer containing a water soluble spacer group between said phobe and the ethylenic unsaturation such that there is an average of at least two phobes extending from the surface of said PNPs, each phobe having an alkyl group with at least four carbon atoms; and at least one solvent;

at least one neutralizing agent to partially neutralize the at least one neutralizable ethylenically-unsaturated monomer; and an aqueous medium, wherein the solvent comprises at least one of isopropanol, alkyl cellosolve, and alkyl carbitol and has a solubility in water of at least 10 weight percent.

9. An associative thickener composition, comprising:
polymeric nanoparticles (PNPs) having a diameter in the range of from 1 to 8.2 nanometers, said PNPs comprising as polymerized units at least one multi-ethylenically-unsaturated monomer and at least one neutralizable ethylenically-unsaturated monomer, and an ethylenically-unsaturated phobe-containing monomer containing a water soluble spacer group between said phobe and the ethylenic unsaturation such that there is an average of at least two phobes extending from the surface of said PNPs, each phobe having an alkyl group with at least four carbon atoms; and at least one neutralizing agent that partially neutralizes the at least one neutralizable ethylenically-unsaturated monomer.

* * * * *